US006936741B2

United States Patent
Münnig et al.

(10) Patent No.: US 6,936,741 B2
(45) Date of Patent: *Aug. 30, 2005

(54) PROCESS FOR WORKING UP THE WASTE WATER OBTAINED IN THE PREPARATION OF DINITROTOLUENE

(75) Inventors: Jürgen Münnig, Kaarst (DE); Dietmar Wastian, Dormagen (DE); Wolfgang Lorenz, Dormagen (DE); Berthold Keggenhoff, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/878,211

(22) Filed: Jun. 28, 2004

(65) Prior Publication Data

US 2004/0262238 A1 Dec. 30, 2004

(30) Foreign Application Priority Data

Jun. 30, 2003 (DE) ........................................ 103 29 304

(51) Int. Cl.$^7$ ............................................. C07C 205/00
(52) U.S. Cl. ........................ 568/934; 568/927; 568/939; 568/940
(58) Field of Search ................................ 568/934, 927, 568/939, 940

(56) References Cited

U.S. PATENT DOCUMENTS

| | | | |
|---|---|---|---|
| 3,742,072 A | 6/1973 | Roth | 260/645 |
| 4,230,567 A | 10/1980 | Larbig | 210/600 |
| 4,241,229 A | 12/1980 | Alexanderson | 568/939 |
| 4,257,986 A | 3/1981 | Milligan et al. | 568/934 |
| 4,597,875 A | 7/1986 | Carr et al. | 210/710 |
| 4,642,396 A | 2/1987 | Carr et al. | 568/934 |
| 5,762,802 A | 6/1998 | Carr et al. | 210/626 |
| 6,254,789 B1 | 7/2001 | Marion et al. | 210/765 |
| 6,288,289 B1 * | 9/2001 | Boyd et al. | 568/934 |
| 6,506,948 B1 | 1/2003 | Sawicki | 568/934 |

* cited by examiner

*Primary Examiner*—J. Parsa
(74) *Attorney, Agent, or Firm*—Joseph C. Gil; N. Denise Brown

(57) ABSTRACT

The present invention relates to a process for working up or treating aqueous waste waters which are formed during the nitration of toluene to dinitrotoluene with nitrating acid. These aqueous waste waters containing acidic wash water and alkaline wash water from the dinitrotoluene washing step, and distillate from the sulfuric acid concentration step. The process comprises, a) combining the acidic and alkaline waste waters from the washing step and the aqueous distillate from the sulfuric acid concentration step such that the resulting mixture has a pH below 5, b) separating the aqueous and organic phases which are formed by phase separation, c) subjecting the aqueous phase from b) to an extraction step, wherein d) the organic components contained in the aqueous phase from c) are extracted with toluene, and e) introducing the toluene phase enriched with the organic components into the toluene nitration.

10 Claims, No Drawings

PROCESS FOR WORKING UP THE WASTE WATER OBTAINED IN THE PREPARATION OF DINITROTOLUENE

BACKGROUND OF THE INVENTION

The present invention provides a process for working up or treating the reaction water and wash water are obtained during the preparation of dinitrotoluene (DNT) by the nitration of toluene. It is necessary to treat the reaction water and wash water to avoid losses of DNT, and to be able to send the process waste water for a biological work-up.

In the conventional processes for the preparation of dinitrotoluene (DNT) from toluene and a mixture of sulphuric acid and nitric acid (nitrating acid), the acidic reaction water distilled off in the sulfuric acid concentration step, and alkaline and acidic wash water from the purification of the DNT, are obtained as aqueous waste waters. In addition to mononitrotoluene and dinitrotoluene, this process waste water contains other nitration by-products such as, for example, mononitrocresols, dinitrocresols and trinitrocresols (hereafter referred to globally as nitrocresols), picric acid and nitrobenzoic acids. There are two main reasons why these substances have to be removed from the aqueous phases. First, with concentrations of DNT up to or exceeding 2.5 wt. % and of MNT as high as 1.5 wt. % being present in the process water, the disposal of the untreated waste water represents a loss of yield of desired product. Second, aromatic nitro compounds do not easily degrade in biological waste water treatment plants and have properties toxic to bacteria.

Different processes have been described in previous studies on the nitration of aromatic compounds with treatment of the aqueous phases formed.

U.S. Pat. No. 6,506,948 describes the nitration of toluene, wherein each of the aqueous phases obtained are extracted directly with toluene. U.S. Pat. No. 6,506,948 does not disclose or suggest settling of the organic materials prior to extraction. In the extraction process of U.S. Pat. No. 6,506,948, the aqueous acidic phases from the sulfuric acid concentration step, as well as an aqueous acidic phase and an aqueous alkaline phase from the DNT washing step, are extracted with toluene, with the toluene stream being introduced into the individual aqueous phases in succession. Then, the toluene stream is processed in the nitration process. Since the various waste waters are treated separately with toluene, each waste water stream requires its own mixer-settler.

U.S. Pat. No. 4,642,396 describes the transfer of nitration products from the aqueous acidic phase to the organic phase in the nitration mixture by the introduction of nitrogen monoxide. Any nitric acid still present is thereby reduced to nitrogen dioxide, which can be converted to nitric acid in a suitable downstream process. However, this process requires the handling of nitrogen dioxide, a substance foreign to the process, which obviously has to be utilized in another plant for the preparation of nitric acid.

The recovery of nitroaromatics (e.g. nitrobenzene) from alkaline wash water by extraction with the educt of the nitration process (benzene) is described in, for example, U.S. Pat. No. 4,241,229. This reference specifically relates to the nitration of benzene to nitrobenzene by the nitrating acid process. It also discloses the separation of nitroaromatics from waste water and wash water by steam stripping. Although it describes the recovery of product, it does not describe or suggest a further treatment of the salts of phenols, picric acid and organic acids which are dissolved in the alkaline wash water.

The treatment of nitrocresols which are separated from the product stream in the alkaline DNT washing step by oxidative degradation with nitric acid at elevated temperatures requires its own separate process stage. This is described in EP-A1-0 962 446.

In the context of the preparation of nitrobenzene, U.S. Pat. No. 4,230,567 likewise describes the degradation of nitrophenol in an additional process step at elevated pressure and temperature.

U.S. Pat. No. 4,597,875 also proposes a process for the separation of nitrocresol components from the dinitrotoluene product and the resulting wash water. Nitrocresols are removed from the DNT phase as water-soluble salts in an extraction step using alkaline wash water. After the separation of DNT, sulfuric or nitric acid is added to the alkaline wash water in order to precipitate the nitrocresol components. Then, after mechanical settling of the nitrocresol phase, the latter can be disposed of in a suitable combustion process. The nitric acid and sulfuric acid feed materials are hereby consumed for separation of the secondary components. A separate disposal of the nitrocresol components is additionally required.

U.S. Pat. No. 4,257,986 provides a process for the treatment of sulfuric acid obtained in the nitration of aromatic compounds with nitrating acid. To remove nitric acid, nitrous acid and organic impurities from this sulfuric acid, the latter is treated with the aromatic compound to be nitrated (educt) and with various reducing or oxidizing agents. This process also requires the use of additional substances which are foreign to the nitration process.

The object of the present invention is to provide a simple and economic process for the recovery of the nitration products contained in the various aqueous waste waters and for the separation and treatment of unwanted secondary components of the nitration. Surprisingly, this is achieved by means of steps that are simple in terms of process technology, compared with existing processes, and without using additional process steps and feed materials which are foreign to the nitration process.

SUMMARY OF THE INVENTION

The present invention relates to a process for working up or treating aqueous waste waters which are obtained in the nitration of toluene to dinitrotoluene with nitrating acid. These aqueous waste waters contain the acidic wash water and the alkaline wash water from the dinitrotoluene washing step, and the distillate from the sulfuric acid concentration step. This process comprises a) combining the acidic and alkaline waste waters from the washing step, and the aqueous distillate from the sulfuric acid concentration step such that the resulting mixture has a pH below 5 as measured at 70° C., b) separating the aqueous and organic phases which are formed from the mixture in a) by phase separation, c) subjecting the aqueous phase from step b) to an extraction step, wherein d) the organic components which are present in the aqueous phase are extracted with toluene, and e) introducing the toluene phase which is enriched with the organic components into the toluene nitration process.

In the conventional process for the nitration of aromatic hydrocarbons, the hydrocarbon is reacted with a mixture of sulfuric acid and nitric acid (i.e. nitrating acid). In the case of the nitration of toluene to dinitrotoluene, a two-stage nitration is one of the generally current processes along with the one-stage nitration process as described in, for example, U.S. Pat. No. 6,528,690, believed to correspond to EP-A2-908 442, the disclosure of which is herein incorporated by reference. In the two-stage process, toluene is first converted to mononitrotoluene (MNT) with nitric acid and sulfuric acid (mono-stage). After separation of the resulting reaction mixture into MNT and an acidic phase, which can be carried out in static settlers or dynamic settlers, the MNT is reacted again with nitric acid and sulfuric acid to give dinitrotoluene (DNT) (di-stage). The sulfuric acid phase from the mono-stage is concentrated. The sulphuric acid feed for the di-stage is concentrated acid. The reaction mixture of the di-stage is separated into an organic phase, i.e. the crude DNT, and an acidic phase, it being possible for the acidic phase to be used as sulfuric acid feed for the mono-stage or concentrated. This reaction mixture of the di-stage can likewise be separated in static or dynamic settlers.

All processes for the preparation of DNT by the nitration of toluene with nitrating acid produce two material streams which have to be sent for a further work-up or treatment. These streams are the crude DNT and the sulfuric acid diluted by the reaction water and by the water present in the nitric acid used.

The crude DNT generally consists substantially of the desired reaction product with up to 1.5 wt. % of sulfuric acid, 0.5 wt. % to 1.2 wt. % of excess nitric acid and up to approx. 1 wt. % of nitration by-products. The secondary components are substantially nitrocresols, picric acid and nitrobenzoic acids. In the conventional process, acids and secondary components are removed from the crude DNT in two to four washing stages with water. The wash water introduced in this process can contain a base in at least one washing stage. Typically, the base used is sodium hydroxide or sodium carbonate in concentrations of 2–10 wt. %. Whereas the neutral aqueous washing step extensively removes sulfuric acid and nitric acid from the nitration product, the alkaline washing step also transfers salt-forming organic components such as, for example, nitrocresols, picric acid and nitrobenzoic acids, to the aqueous phase.

Other than for the one-stage alkaline washing step and the last aqueous washing step, fresh water or wash water from a subsequent stage, introduced in countercurrent, can be used as wash water. However, the wash water used can also be fresh water, demineralized water or any other water of suitable quality from a subsequent process to the nitration process described.

The amounts of wash water used for the washing steps are preferably from 15 to 90 parts by weight, and more preferably from 50 to 65 parts by weight of wash water, per 100 parts by weight of DNT.

Depending on the quantity of wash water used and the source of the wash water feed, the neutral aqueous washing step produces an acidic process waste water having preferred acid contents of 1.0 to 3.0 wt. % of nitric acid and 2.0 to 6.0 wt. % of sulfuric acid and a DNT content of several thousand ppm. The concentration of organic nitration by-products (i.e. organic secondary components) in the process waste water is generally between 300 and 900 ppm.

The waste water stream of the alkaline washing step generally contains 3.0 to 7.0 wt. % of organic nitration by-products, which consist substantially of nitrocresols, picric acid and nitrobenzoic acids, in the form of their water-soluble salts of the base which was used. This waste water stream can further contain several thousand ppm of DNT, together with 2.0–4.0 wt. % of nitric acid and approx. 0.6–1.2 wt. % of sulfuric acid in the form of their water-soluble salts. The waste water stream of the alkaline washing step has a pH of >7.0, and preferably of >7.5, as measured at 80° C.

The washing stages are carried out in suitable apparatuses and preferably in scrubber or extraction columns or in mixer-settlers.

The dilute sulfuric acid from the nitration can comprise 70–90 wt. %, preferably 70–80 wt. % and most preferably 75–79 wt. % of sulfuric acid. It can also contain 0.005–0.5 wt. % and preferably 0.005–0.05 wt. % of nitric acid, and up to 3.0 wt. % of MNT, and 0.2–2.0 wt. % of DNT. The acid to be worked up also contains up to 0.2 wt. % of organic secondary components consisting substantially of nitrocresols, picric acid and nitrobenzoic acids. Examples of possible processes for concentration of the dilute sulfuric acid are, inter alia, the Pauling process at normal pressure [as described by, for example, Bodenbrenner, von Plessen, Vollmüller, Dechema-Monogr. 86 (1980), 197], which produces approx. 97% sulfuric acid, and vacuum evaporation as described in U.S. Pat. No. 6,332,949, believed to correspond to DE-A1-196 42 328, the disclosure of which is herein incorporated by reference, which can also yield up to 97% sulfuric acid. As well as the desired sulfuric acid, one or more aqueous phases with a sulfuric acid content of 0.2 to 1.0 wt. % and preferably of 0.2 to 0.6 wt. %, an MNT content of 0.7 to 7.0 wt. %, and a DNT content of 2.0 to 6.0 wt. % are generally obtained after condensation of the vapors. Other organic compounds are conventionally present in concentrations of up to 0.4 wt. %. The organic components in the distillate are dissolved or dispersed.

In the process according to the invention, the waste water streams of the neutral and alkaline DNT washing steps and the sulfuric acid concentration step are combined. The aqueous phases from the nitration are made up of several individual streams, preferably two to four, at least one of the individual streams originating from the neutral aqueous washing step (acidic wash water) and at least one individual stream originating from the alkaline washing step (alkaline wash water). The aqueous phases from the sulfuric acid concentration step are made up of one or more individual streams with said contents of acids and organic components.

The process waste water streams can be combined in an appropriate tank with a dynamic mixing element, or, for example, by means of a static mixing unit. After the streams have been combined, the pH of the resulting mixture is below 5 as measured at 70° C., and preferably below 2. From this mixture, an organic phase settles out. If the alkaline washing step is carried out with very large amounts of base, it is theoretically possible to obtain a pH of ≧5 when the waste waters from the DNT washing step and the distillate from the sulfuric acid concentration step are combined. The amount of alkaline waste water used, for example, would then have to be reduced accordingly in order to bring the pH below 5. This organic phase consists of MNT and DNT together with nitration by-products. These nitration by-products are predominantly nitrocresols, picric acid and nitrobenzoic acids. If carbonate is used in the alkaline washing step, there must be an appropriate venting facility at, or close to the point where the streams are combined. To separate off the organic phase which is formed, the combined waste water streams are then sent to a suitable settling vessel.

The advantage of the process according to the present invention is that, by combining the various acidic and alkaline process waste water streams, the nitration by-products, which are predominantly nitrocresols, picric acid and nitrobenzoic acids, can be settled out as a separate organic phase without one of the acid feeds of the nitration process additionally being consumed for this purpose. Also, after these process waste waters have been combined, only one waste water stream has to be sent for a further work-up.

MNT can additionally be fed in when the process waste water streams are combined. The addition of MNT can assist the phase separation, and by lowering the solidification point of the organic phase, can facilitate the transportation of this mixture of materials in the process. The amounts of MNT added are preferably 0.2 to 9.0 parts by weight, and more preferably 0.5 - to 4.0 parts by weight of MNT, per 100 parts by weight of process waste water.

Because of the density differences, the organic phase, which consists predominantly of MNT, DNT, nitrocresols, picric acid and nitrobenzoic acids, conventionally forms the heavier phase. This organic phase can be removed from the settling vessel and disposed of, e.g., by combustion. Preferably, however, these organic materials are recycled back into the nitration process.

The aqueous phase from the settler is subjected to extraction of the waste water. This aqueous phase generally contains organic components in the following concentration ranges: from 50 to 1000 ppm of MNT, from 100 to 3000 ppm of DNT, and from 100 to 3000 ppm of nitrocresols, picric acid and nitrobenzoic acids, taken together. It also contains sulphuric acid and nitric acid in concentrations of 0.4 to 2.0 wt. %, of each acid.

This aqueous phase is extracted with toluene, which is the nitration educt. The extraction is carried out in appropriate mixer-settler units or pulsed packed columns and sieve-plate columns, but preferably in stirred multistage extraction columns, with the toluene and the aqueous phase being circulated in countercurrent fashion. This extraction can be operated in a single extraction column, or in several extraction columns running in parallel. The extraction agent can be introduced directly into the extraction column. In addition, toluene can be passed via a static mixer unit into the aqueous phase before introduction of the aqueous phase into the extraction apparatus. The weight ratio of toluene to aqueous phase can range from 33:100 to 5:100 and preferably from 33:100 to 10:100. Surprisingly, this extraction procedure makes it possible to reduce the concentration of nitration products and organic by-products in the aqueous phase to below 10 ppm of MNT and DNT, and below 1000 ppm and preferably below 200 ppm of nitrocresols, picric acid and nitrobenzoic acids, with approx. 500–2000 ppm of toluene generally being absorbed into the aqueous phase.

The toluene stream from the extraction is then preferably introduced into the nitration process as a raw material.

The aqueous phase obtained from the extraction conventionally contains approx. 500 to 2000 ppm of toluene. This toluene can be removed from the aqueous phase by steam stripping, wherein, for example, the aqueous phase is introduced into the top of a stripper column. The column is operated at a pressure preferably of 200 to 400 mbar and more preferably of 200 to 300 mbar. Steam at an appropriate pressure, preferably 2–6 bar, is introduced into the lower part of the column. Between the point of introduction of the aqueous phase and the steam feed, the column is preferably provided with structured or random packing or plates. Surprisingly, the waste water treated in this way contains toluene concentrations of below 10 ppm.

The toluene brought into the steam stripper with the aqueous phase vaporizes in the stripper column and is condensed together with steam. Among other possible uses, the toluene/water mixture obtained in this way can be recycled for waste water extraction, or subjected to a phase separation, after which the toluene that has settled out can be recycled into the nitration.

The following examples further illustrate details for the process according to the invention. The invention, which is set forth in the foregoing disclosure, is not to be limited either in spirit or scope by these Examples. Thos skilled in the art will readily understand that known variations of the conditions of the following procedures can be used. Unless otherwise noted, all temperatures are degrees Celcius and all percentages are percentages by weight.

EXAMPLES

Example 1

Combining of the Process Waste Water Streams with Phase Separation and Settling-Out of the Aqueous Phase from the Organic Phase:

62.07 kg/h of process water from the sulfuric acid concentration step (Stream A), 22.08 kg/h of acidic wash water (Stream B) and 6.13 kg/h of alkaline wash water from the DNT washing step (Stream C), at an average temperature of 70° C., were passed through a common waste water manifold and a static in-line wash water mixer into a settler for organic materials. This settler consisted of a horizontal tank with a diameter of 100 mm and a length of 600 mm. The tank was equipped with an internal overflow weir. From the continuously operating settling vessel, 86.73 kg/h of process waste water freed of undissolved organic components (Stream D) were withdrawn in the overflow as the lighter phase. The organic materials separated off (Stream E) constituted the heavier phase and were withdrawn from the settler at the bottom.

TABLE 1

| Component | Stream A [kg/h] | Stream B [kg/h] | Stream C [kg/h] | Stream D [kg/h] | Stream E [kg/h] |
|---|---|---|---|---|---|
| MNT | 1.10 | 0.00 | 0.00 | 0.01 | 1.09 |
| DNT | 1.76 | 0.18 | 0.05 | 0.03 | 1.96 |
| NITROCRESOLS, PICRIC ACID, NITROBENZOIC ACIDS | 0.22 | 0.01 | 0.31 | 0.05 | 0.49 |
| $HNO_3$ | 0.18 | 0.24 | 0.00 | 0.40 | 0.00 |
| $HNO_2$ | 0.05 | 0.03 | 0.00 | 0.08 | 0.00 |
| $H_2SO_4$ | 0.13 | 0.61 | 0.00 | 0.73 | 0.00 |
| $H_2O$ | 58.63 | 20.97 | 5.43 | 85.03 | 0.00 |
| $Na_2CO_3$ | 0.00 | 0.00 | 0.02 | 0.00 | 0.00 |
| $Na_2SO_4$ | 0.00 | 0.00 | 0.08 | 0.09 | 0.00 |
| $NaNO_3$ | 0.00 | 0.00 | 0.23 | 0.25 | 0.00 |
| $CO_2$ | 0.00 | 0.04 | 0.01 | 0.06 | 0.00 |
| $N_2$ | 0.00 | 0.00 | 0.00 | 0.00 | 0.00 |
| Mass stream [kg/h] | 62.07 | 22.08 | 6.13 | 86.73 | 3.54 |

Example 2

Waste Water Extraction with Toluene:

Waste water from the settling vessel (Stream F) was introduced at a rate of 90.54 kg/h and at a temperature of 70° C. into the upper part of a stirred extraction column with a diameter of 100 mm and a length of 800 mm. 16.9 kg/h of toluene (Stream G) at 30° C. were introduced into the lower part of the column according to the countercurrent principle. When the extraction process was finished, the density difference was such that the toluene phase (Stream H) overflowed at the top of the column into a receiver. The purified waste water stream (Stream I) emerged from the bottom of the column and could be sent to the steam stripper.

TABLE 2

| Component | Stream F [kg/h] | Stream G [kg/h] | Stream H [kg/h] | Stream I [kg/h] |
|---|---|---|---|---|
| TOLUENE | 0.00 | 16.90 | 16.83 | 0.07 |
| MNT | 0.01 | 0.00 | 0.01 | 0.00 |
| DNT | 0.03 | 0.00 | 0.03 | 0.00 |
| NITROCRESOLS, PICRIC ACID, NITROBENZOIC ACIDS | 0.05 | 0.00 | 0.04 | 0.01 |
| $HNO_3$ | 0.44 | 0.00 | 0.00 | 0.44 |
| $HNO_2$ | 0.09 | 0.00 | 0.00 | 0.09 |
| $H_2SO_4$ | 0.73 | 0.00 | 0.00 | 0.73 |
| $H_2O$ | 88.79 | 0.00 | 0.03 | 88.76 |
| $Na_2SO_4$ | 0.09 | 0.00 | 0.00 | 0.09 |
| $NaNO_3$ | 0.25 | 0.00 | 0.00 | 0.25 |
| $CO_2$ | 0.06 | 0.00 | 0.00 | 0.06 |
| Mass stream [kg/h] | 90.54 | 16.90 | 16.94 | 90.50 |

Example 3

Separation of Toluene by Steam Stripping:

A waste water (Stream J) from the bottom of the waste water extraction column was introduced continuously at a rate of 502.24 kg/h, at a temperature of 60° C. and at atmospheric pressure into the top of a stripper column with a diameter of 100 mm and a total height of 1000 mm. The middle part of the column was provided with a packing. 20.1 kg/h of steam at 2.5 bar were fed into the lower part of the column. 501.17 kg/h of purified waste water (Stream K) at a temperature of 60–62° C. were withdrawn from the bottom of the column. A vapor (Stream L) was withdrawn from the top of the stripper column at a pressure of 200 bar and at 58 to 60° C. This stream was condensed with a condenser and a cold trap upstream from the vacuum pump.

TABLE 3

| Component | Stream J [kg/h] | Stream K [kg/h] | Stream L [kg/h] |
|---|---|---|---|
| TOLUENE | 0.37 | 0.00 | 0.37 |
| $HNO_3$ | 2.46 | 2.25 | 0.21 |
| $HNO_2$ | 0.49 | 0.45 | 0.04 |
| $H_2SO_4$ | 4.05 | 4.05 | 0.00 |
| $H_2O$ | 492.95 | 492.52 | 20.53 |
| $Na_2SO_4$ | 0.52 | 0.52 | 0.00 |
| $NaNO_3$ | 1.39 | 1.39 | 0.00 |
| Mass stream [kg/h] | 502.24 | 501.17 | 21.17 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for treating aqueous waste waters formed during the nitration of toluene to dinitrotoluene with nitrating acid, wherein the aqueous waste waters comprise the acidic wash water and alkaline wash water from the dinitrotoluene washing step and the distillate from the sulfuric acid concentration step, comprising a) combining (1) the acidic and alkaline waste waters from the washing step and (2) the aqueous distillate from the sulfuric acid concentration step such that the resultant mixture has a pH below 5, b) separating the resultant aqueous and organic phases by phase separation, c) extracting the organic components present in the aqueous phase resulting from b) with toluene, and d) introducing the toluene phase enriched with the organic components into the toluene nitration.

2. The process of claim 1, wherein a) combining of the aqueous waste waters is in a mixer with a venting facility.

3. The process of claim 1, additionally comprising mixing the combined aqueous phases with mononitrotoluene.

4. The process of claim 1, additionally comprising recycling the organic phase from b) into the nitration process.

5. The process of claim 1, wherein the aqueous phase from step b) is mixed with toluene in a static mixer before c) extracting the organic components.

6. The process of claim 1, wherein the aqueous phase from b) and toluene are introduced into c) in countercurrent fashion for said extraction step and are present in a weight ratio of toluene to aqueous phase of 33:100 to 5:100.

7. The process of claim 1, wherein c) extracting the organic components with toluene is carried out in stirred multistage extraction columns.

8. The process of claim 1, additionally comprising steam stripping the aqueous phase resulting from said extraction, thereby removing the toluene from the aqueous phase to yield a water/toluene mixture.

9. The process of claim 8, wherein the steam stripping is carried out with a stripper column provided with structured or random packing or plates, and the aqueous phase in introduced into the top of the stripper column and the steam is fed into the lower region of the column.

10. The process of claim 8, additionally comprising recycling the resultant water/toluene mixture c) the extraction or into the nitration process.

* * * * *